(12) United States Patent
Ray et al.

(10) Patent No.: US 10,888,287 B2
(45) Date of Patent: Jan. 12, 2021

(54) IMAGING DEVICE

(71) Applicant: Omega Medical Imaging, LLC, Sanford, FL (US)

(72) Inventors: Mark Ray, Sanford, FL (US); Charlie Yuan, Lake Mary, FL (US); Chris Henning, Deltona, FL (US); Thomas Gribben, Orlando, FL (US); Jeffrey C. Schmidt, Orlando, FL (US); Brian Fleming, Lake Mary, FL (US)

(73) Assignee: OMEGA MEDICAL IMAGING, LLC, Sanford, FL (US)

( * ) Notice: Subject to any disclaimer, the term of this patent is extended or adjusted under 35 U.S.C. 154(b) by 45 days.

(21) Appl. No.: 16/351,094

(22) Filed: Mar. 12, 2019

(65) Prior Publication Data

US 2020/0289073 A1    Sep. 17, 2020

(51) Int. Cl.
*A61B 6/00* (2006.01)

(52) U.S. Cl.
CPC .......... *A61B 6/4441* (2013.01); *A61B 6/4208* (2013.01); *A61B 6/4452* (2013.01); *A61B 6/588* (2013.01)

(58) Field of Classification Search
CPC ... A61B 6/4482; A61B 6/4452; A61B 6/4405; A61B 6/4435; A61B 6/035
See application file for complete search history.

(56) References Cited

U.S. PATENT DOCUMENTS

| | | |
|---|---|---|
| 3,000,473 A | 9/1961 | Reynolds |
| 3,244,292 A | 4/1966 | Elliott |
| 3,268,092 A | 8/1966 | Hainner et al. |
| 3,305,220 A | 2/1967 | Nevulis |
| 3,480,109 A | 11/1969 | Eitel et al. |
| 4,051,525 A | 9/1977 | Kelly |
| 4,303,237 A | 12/1981 | Hoffend, Jr. et al. |
| 5,056,278 A | 10/1991 | Atsukawa |
| 5,102,375 A | 4/1992 | Featherstone |
| 5,138,647 A * | 8/1992 | Nguyen ............... A61B 6/4225 378/189 |
| 5,238,287 A | 8/1993 | Haddad, Jr. |
| 5,557,892 A | 9/1996 | Lavin |
| 6,041,558 A | 3/2000 | Sylvestre |
| 6,224,037 B1 | 5/2001 | Novick |

(Continued)

FOREIGN PATENT DOCUMENTS

| | | |
|---|---|---|
| DE | 102014221469 A1 | 4/2016 |
| EP | 1028482 A2 | 8/2000 |
| JP | H06327662 A | 11/1994 |

OTHER PUBLICATIONS

Soma Technology, Inc., "Siemens Arcadia Varic C-Arm," https://www.somatechnology.com/C-Arms/Siemens-Arcadis-Varic.aspx, Mar. 13, 2019, 2 pages.

(Continued)

*Primary Examiner* — Don K Wong
(74) *Attorney, Agent, or Firm* — Tucker Ellis LLP; Patrick F. Clunk

(57) ABSTRACT

Provided is an imaging device including a body, an x-ray detector assembly attached to the body, and an x-ray source assembly attached to the body. The x-ray detector assembly includes a telescopic actuator movable between a retracted position and an extended position, and an x-ray detector attached to the telescopic actuator.

19 Claims, 12 Drawing Sheets

(56) References Cited

U.S. PATENT DOCUMENTS

| | | |
|---|---|---|
| 6,244,450 B1 | 6/2001 | Woodling |
| 6,253,502 B1 | 7/2001 | Layton |
| RE37,559 E | 2/2002 | Marue et al. |
| 6,447,150 B1 | 9/2002 | Schneider et al. |
| 6,789,941 B1 | 9/2004 | Grady |
| 7,300,205 B2 | 11/2007 | Grady |
| 7,497,140 B2 | 3/2009 | Blackwelder et al. |
| 7,574,832 B1 | 8/2009 | Lieberman |
| 7,735,808 B2 | 6/2010 | Guarro et al. |
| 8,011,098 B2 | 9/2011 | Vorhies et al. |
| 8,276,326 B2 | 10/2012 | Lounis et al. |
| 8,671,626 B1 | 3/2014 | Marty et al. |
| 2006/0086566 A1 | 4/2006 | Linsmeier et al. |
| 2007/0140436 A1 | 6/2007 | Perry et al. |
| 2009/0159549 A1 | 6/2009 | Trede et al. |
| 2010/0101086 A1 | 4/2010 | Amram |
| 2016/0287196 A1 | 10/2016 | Fadler et al. |
| 2017/0135667 A1* | 5/2017 | Becker ................. A61B 6/4464 |

OTHER PUBLICATIONS

Siemens Healthineers, "Cios Spin," https://www.healthcare.siemens.com/surgical-c-arms-and-navigation/mobile-c-arms/cios-spin, Mar. 13, 2019, 5 pages.
European Search Report for the corresponding EP Application No. 20162816.1, dated Aug. 3, 2020, 13 pages.

* cited by examiner

US 10,888,287 B2

IMAGING DEVICE

FIELD OF INVENTION

The present invention relates generally to an imaging device, and more particularly to an x-ray imaging device.

BACKGROUND

An imaging device can be used to facilitate fluoroscopy x-ray procedures. Fluoroscopy is a type of medical imaging that generates a continuous X-ray image on a monitor. During a fluoroscopy procedure, an X-ray beam is passed through the body. The image is transmitted to a display so the movement of a body part or of a medical instrument or contrast agent through the body can be observed. These procedures require a high degree of image articulation, which requires fine control of an x-ray source and x-ray detector to generate the required view of the area of the region of interest.

SUMMARY OF INVENTION

The present application provides an imaging device including a body, an x-ray detector assembly attached to the body, and an x-ray source assembly attached to the body. The x-ray detector assembly includes a telescopic actuator movable between a retracted position and an extended position, and an x-ray detector attached to the telescopic actuator. Movement of the telescopic actuator is within an area of the body to increase the working envelop of the imaging device while minimizing the footprint of the imaging device.

In accordance with an aspect of the application, an imaging device is provided that includes a body, an x-ray detector assembly attached to the body, the x-ray detector assembly including a telescopic actuator attached to and movable relative to the body, the telescopic actuator including a base section fixed relative to the body and a plurality of movable telescopic sections that are disposed within the base section in a retracted position and movable relative to the base section to an extended position and a plurality of intermediate positions therebetween, and an x-ray detector attached to and movable with the movable telescopic sections, and an x-ray source assembly attached to the body.

In accordance with another aspect of the application, an imaging device is provided that includes a C-arm having an inner curved surface and an outer curved surface, an x-ray detector assembly attached to the C-arm, the x-ray detector assembly including a telescopic actuator attached to and movable relative to the C-arm and an x-ray detector attached to and movable with the telescopic actuator, the telescopic actuator being attached to the C-arm such that all movement of the telescopic actuator is within an area formed within the inner curved surface of the C-arm, and an x-ray source assembly attached to the C-arm.

In accordance with still another aspect of the application, an imaging system is provided that includes an attachment arm, a pivot assembly rotatably attached to the attachment arm, and an imaging device attached to the pivot assembly, the imaging device including a C-arm, an x-ray detector assembly attached to the C-arm, the x-ray detector assembly including a telescopic actuator attached to and movable relative to the C-arm and an x-ray detector attached to and movable with the telescopic actuator, and an x-ray source assembly attached to the C-arm.

The foregoing and other features of the application are described below with reference to the drawings.

DETAILED DESCRIPTION

Figure 1:
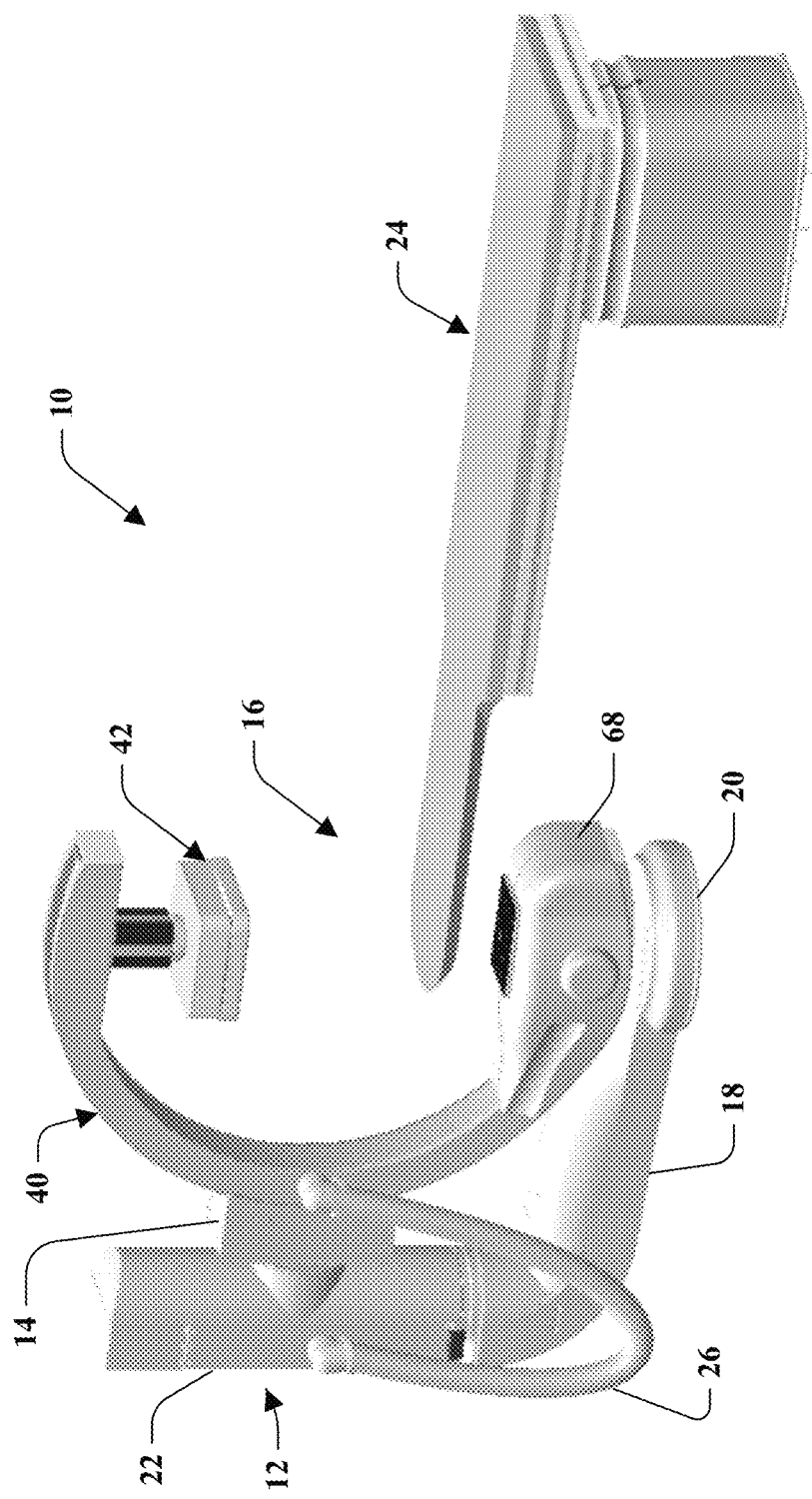
FIG. 1 is a perspective view of an exemplary imaging system and patient table.
Figure 4:
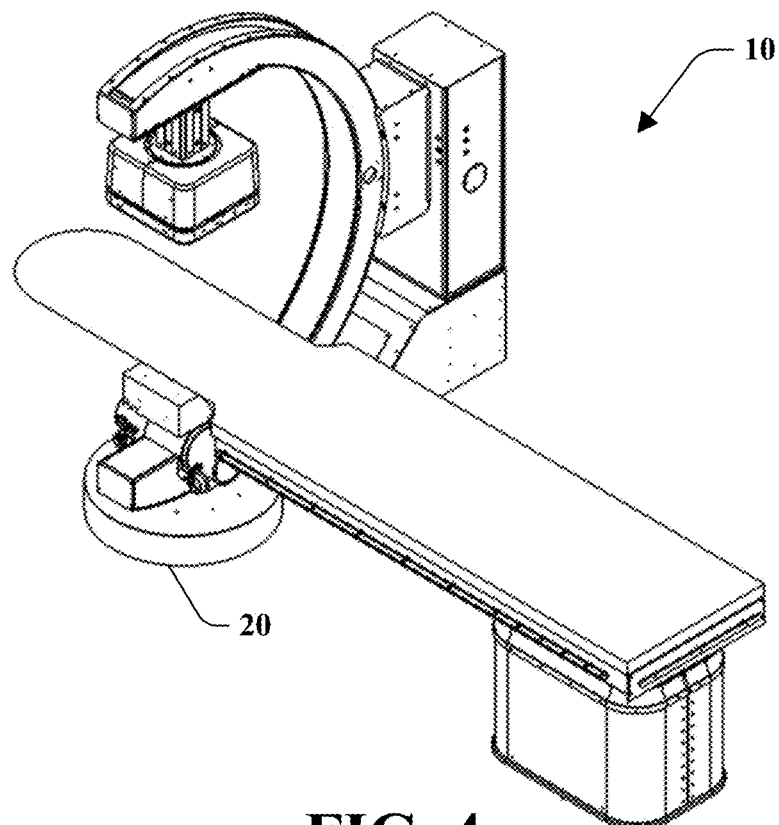
FIG. 4 is a perspective view of the imaging system and patient table with the imaging system rotated at its base.
Figure 5:
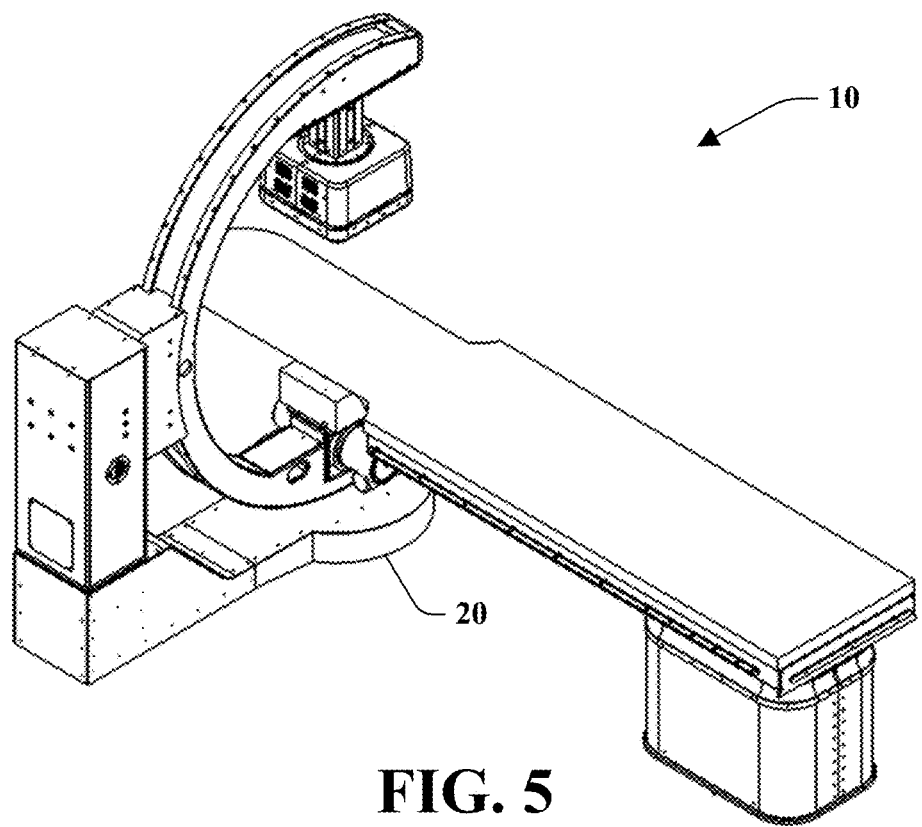
FIG. 5 is another perspective view of the imaging system and patient table with the imaging system rotated at its base.

Turning initially to FIG. 1, an imaging system is shown generally at reference numeral 10. FIGS. 2-15 shown an imaging system or components thereof that are substantially the same as the imaging system in FIG. 1, and consequently the same reference numerals and description apply to both imaging systems. The imaging system includes an attachment arm 12, sometimes referred to as an L-arm, a pivot assembly 14 rotatably attached to the attachment arm 12, and an imaging device 16 attached to the pivot assembly 14 to rotate with the pivot assembly 14 and move relative to the pivot assembly 14. The attachment arm 12 includes a lower portion 18 having a base 20 rotatably attached to a floor of a room, and an upper portion 22 extending upward from the lower portion 18. The base is rotatable about an axis perpendicular to the floor to move the attachment arm 12 around a patient, examples of which are shown in FIGS. 4 and 5.

Figure 2:
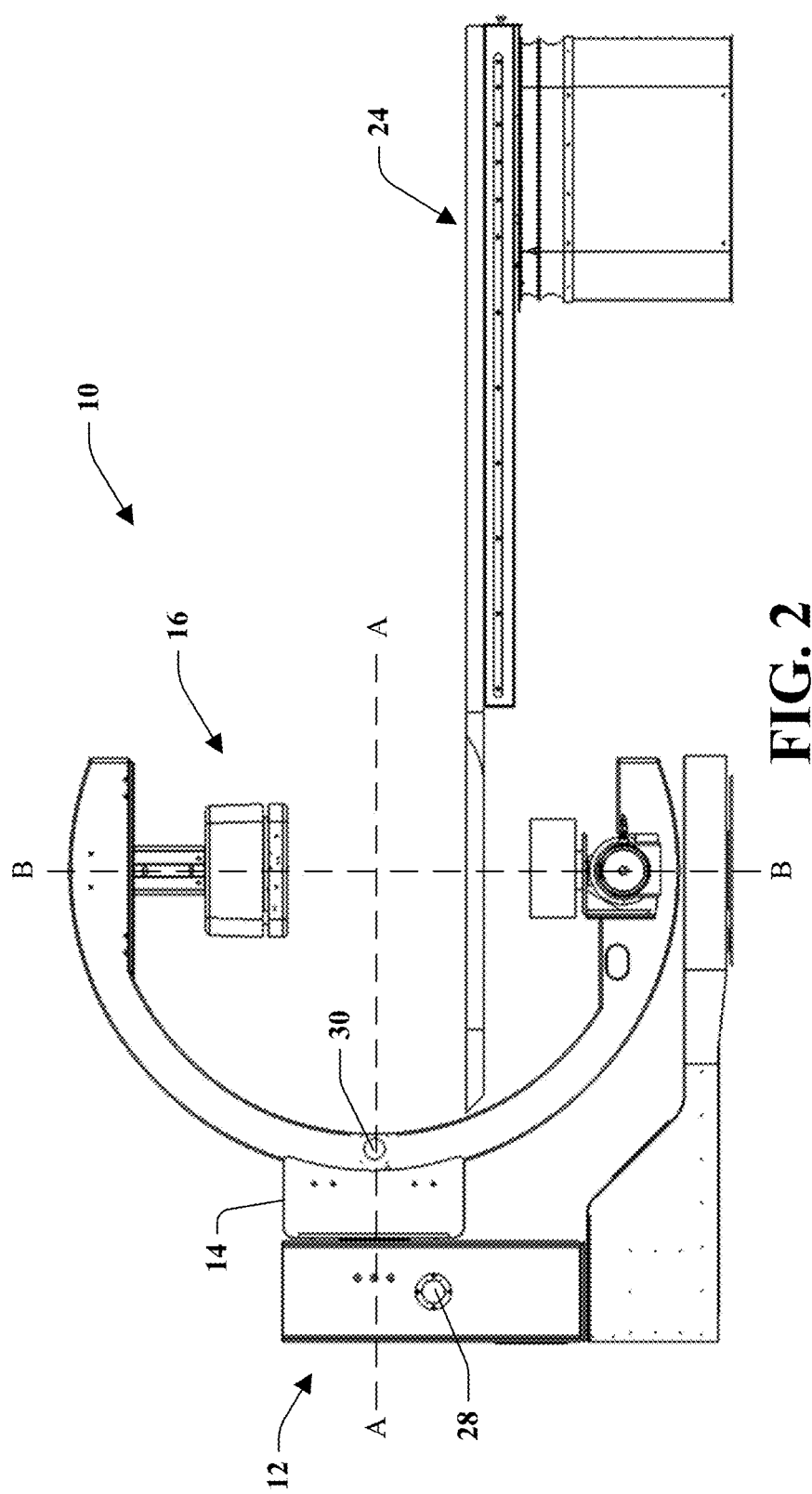
FIG. 2 is a side view of another exemplary imaging system and patient table with a detector in a retracted position.
Figure 3:
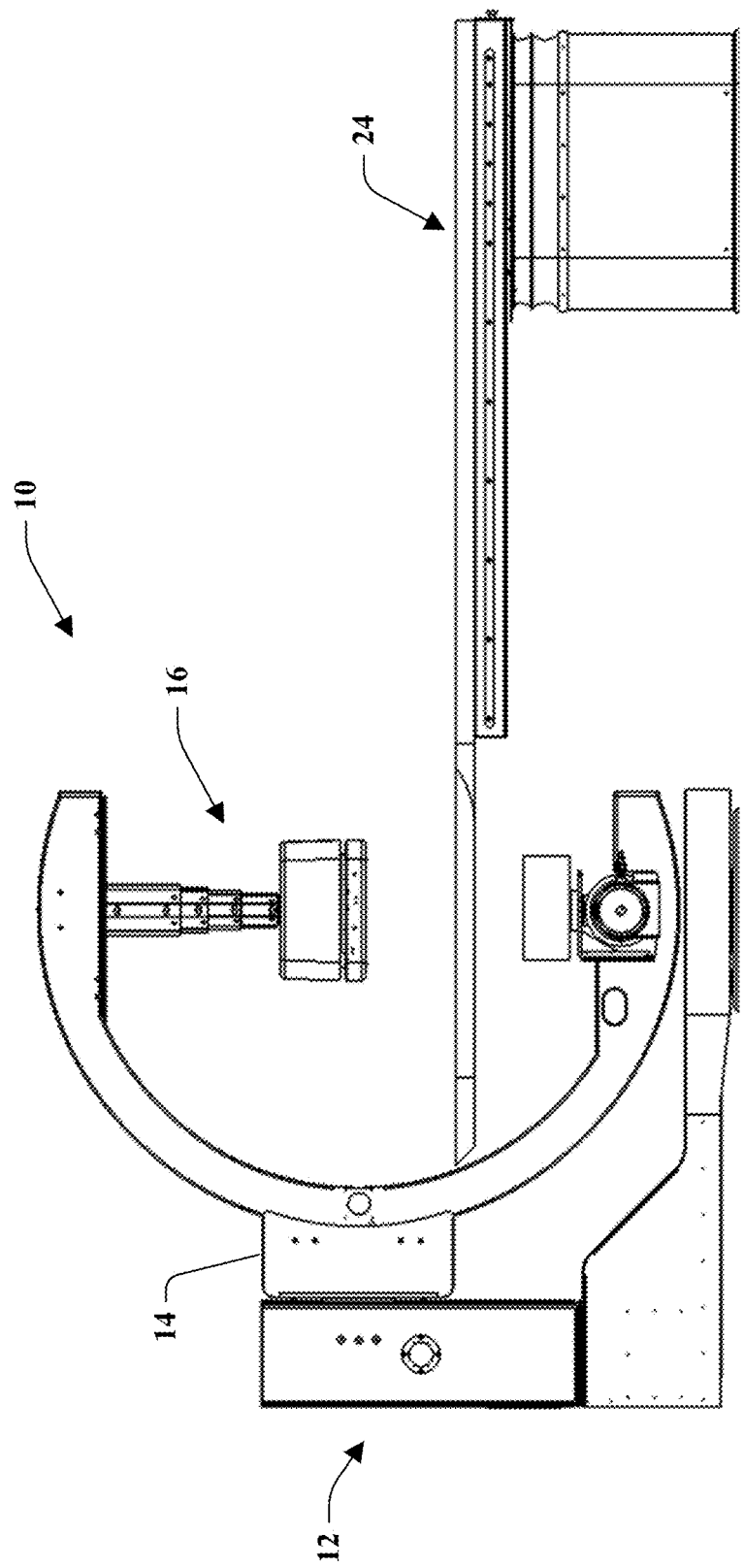
FIG. 3 is a side view of the imaging system and patient table with the detector in an extended position.
Figure 6:
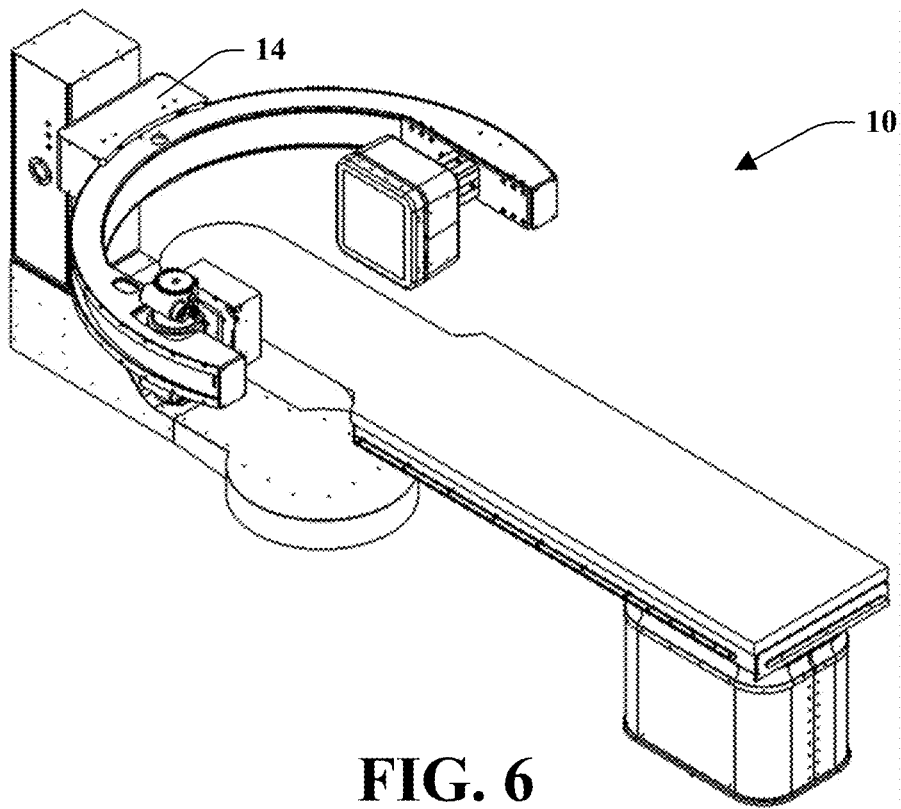
FIG. 6 is a perspective view of the imaging system and patient table with an imaging device rotated at a pivot assembly.
Figure 7:
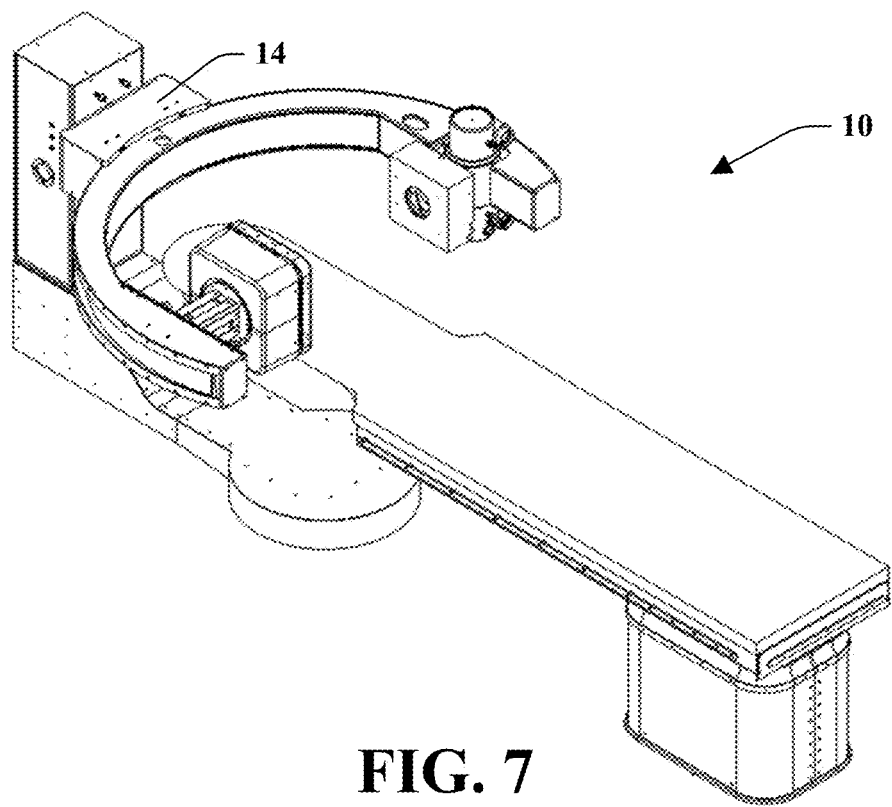
FIG. 7 is another perspective view of the imaging system and patient table with the imaging device rotated at the pivot assembly.
Figure 8:
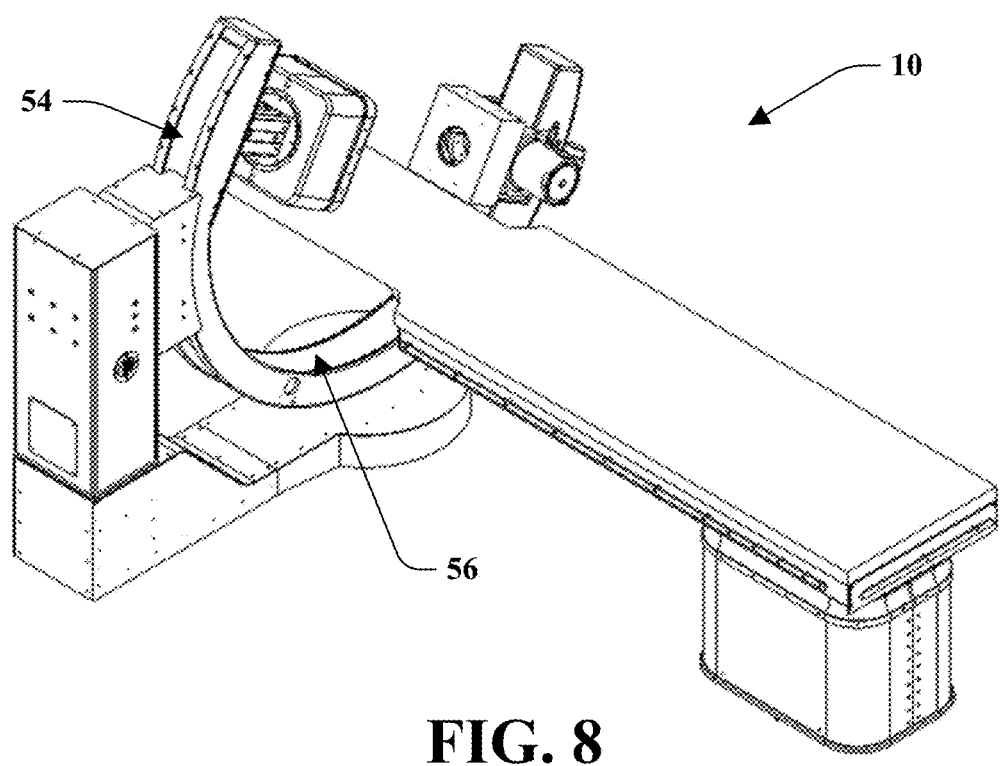
FIG. 8 is a perspective view of the imaging system and patient table with the imaging device moved along its arc.
Figure 9:
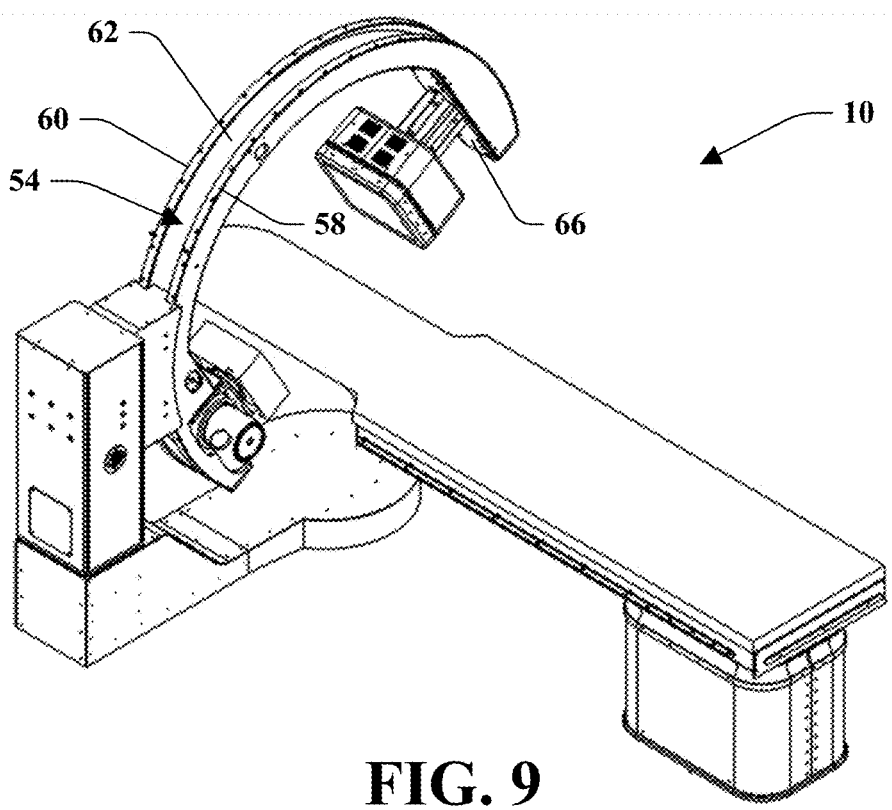
FIG. 9 is another perspective view of the imaging system and patient table with the imaging device moved along its arc.

The pivot assembly 14 is attached to the upper portion 22 of the attachment arm 12 in a suitable manner to rotate about an axis A-A extending through the pivot assembly 14 parallel to the floor. The pivot assembly 14 rotates relative to the upper portion 22 to rotate the imaging device 16 around the patient, examples of which are shown in FIGS. 6 and 7. The imaging device 16 is also attached to the pivot assembly 14 in a suitable manner that allows the imaging device 16 to move along its arc relative to the pivot assembly 14, examples of which are shown in FIGS. 8 and 9. A patient table 24 can be positioned near the imaging device 12, and the imaging device moved relative to the table 14 as shown in FIGS. 4-9. FIG. 2 also shows an isocenter, which is a point in space where the source to axis beam always intersects regardless of the body 40 position. The isocenter is shown as the intersection of the axis B-B of an x-ray detector of an x-ray detector assembly and an x-ray source assembly and the axis A-A of device angulation.

The system also includes a conduit 26 that is connected to the upper portion 22 of the attachment arm 12, such as at opening 28, and connected to the imaging device 16, such as at opening 30. The conduit 26, which may be any suitable conduit, is provided to house electrical wires, control wires, etc. running through the attachment arm 12 and the imaging device 16. It will be appreciated that the upper portion 22 of the attachment arm 12 may include openings at either side to allow for left hand or right hand conduit configuration, for example as shown in FIGS. 4 and 5. If one of the openings is not used for connection of the conduit 26, it can be covered, for example by a plate.

Figure 10:
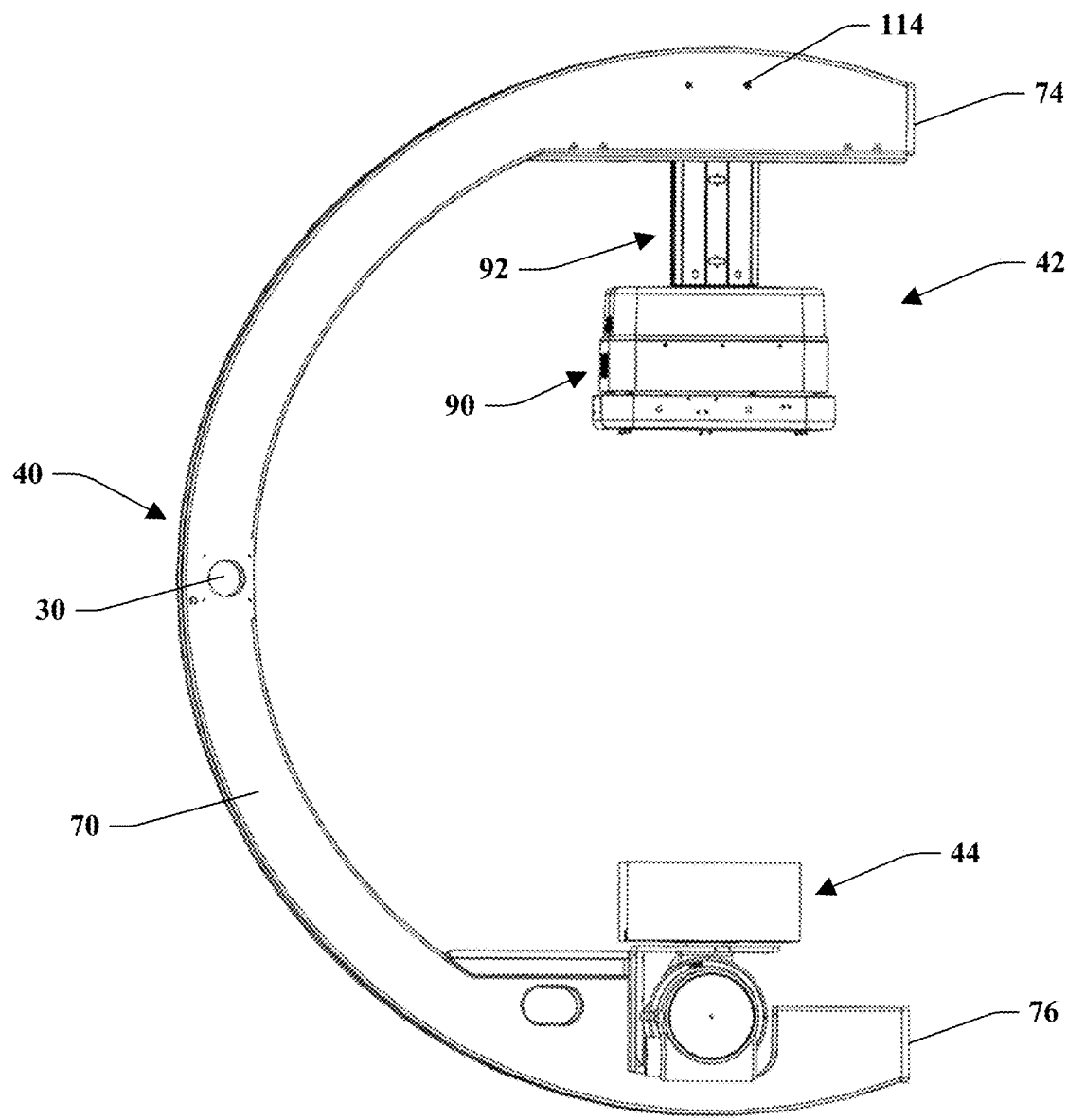
FIG. 10 is a left side view of the exemplary imaging device with an x-ray detector assembly in a retracted position.
Figure 11:
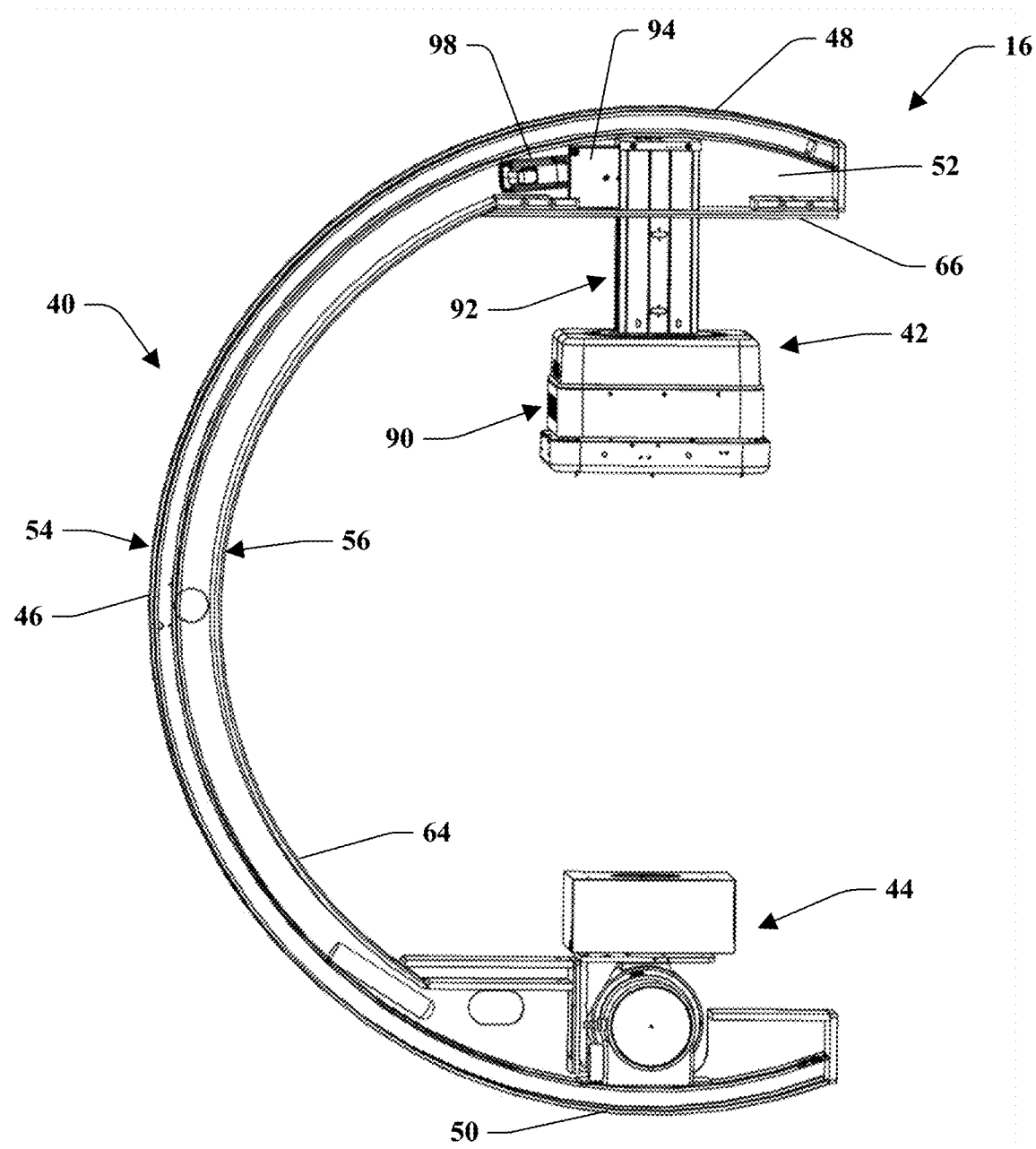
FIG. 11 is a left side view of the imaging device with a side plate removed.
Figure 12:
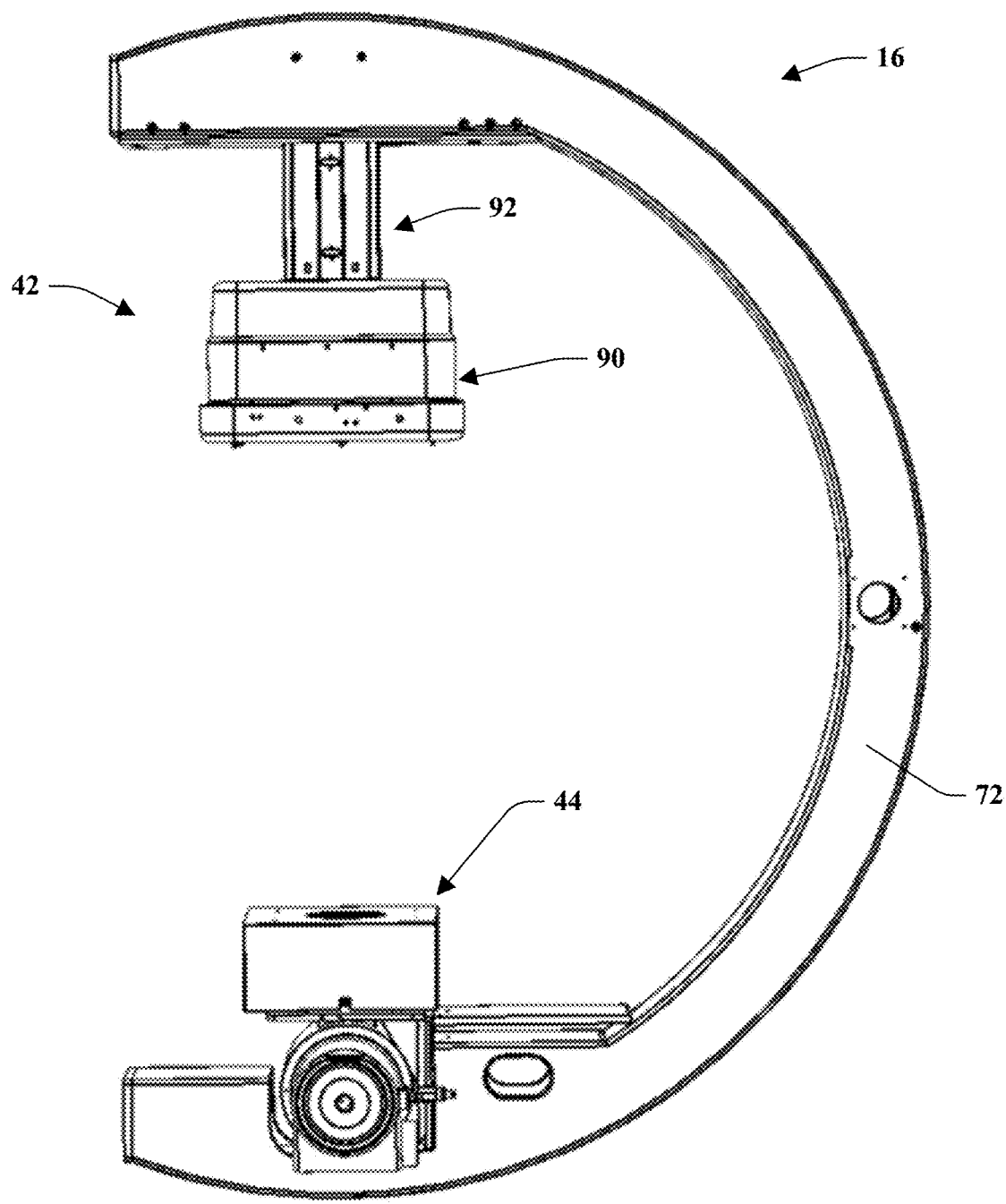
FIG. 12 is a right side view of the exemplary imaging device.

Turning additionally to FIGS. 10-12, the imaging device 16 will now be discussed in detail. The imaging device 16 includes a body 40, an x-ray detector assembly 42 attached to and movable relative to the body 40, and an x-ray source assembly 44 attached to the body 40. In the illustrated embodiment, the body 40 is a C-arm that is substantially C-shaped and has a central portion 46, a first or upper portion 48 extending from the central portion 46, and a second or lower portion 50 extending from the central portion 46. The x-ray detector assembly 42 is attached to the body 40 at the first portion 48 and the x-ray source assembly 44 is attached to the body 40 at the second portion 50. As shown in FIG. 11, the body 40 has a hollow area 52 extending throughout the body 40. The hollow area 52 provides a space for certain components of the x-ray detector assembly 42 to be housed within the hollow area 52 and for the components in the conduit 26, such as electrical and control wires, to be connected to the x-ray detector assembly 42 and the x-ray source assembly 44 to assist in minimizing a footprint of the imaging device 16.

The body 40 has an outer portion 54 attached to the pivot assembly 14 and an inner portion 56 defining an inner area for the patient and for the x-ray detector assembly 42 to move. As shown in FIG. 9, the outer portion 54 includes first and second rails 58 and 60 and an outer cover 62 recessed relative to the first and second rails 58 and 60 to define a track for receiving the pivot assembly 14. The body 40 can move relative to the pivot assembly 14 as shown for example in FIGS. 8 and 9 such that the track moves relative to the portion of the pivot assembly 14 in the track. The inner portion 56 includes an inner cover 64, an upper cover 66, and a lower cover 68 (FIG. 1) that houses the x-ray source assembly 44. As shown in FIG. 11, the upper cover 66 can overlap the inner cover 64 at one end, and as shown in FIG. 1, the lower cover 68 can overlap the inner cover 64 at its other end. The outer portion 54 and inner portion 56 form outer and inner curved surfaces of the central portion, upper portion, and lower portion.

The body 40 also includes first and second side plates 70 and 72 that are substantially C-shaped, a top end plate 74 attached to the side plates 70 and 72 and a bottom end plate 76 attached to the side plates 70 and 72. One of the first and second side plates 70 and 72, and as illustrated side plate 70, includes the opening 30 to which the conduit 26 is attached. The other of the first and second plates 70 and 72 may also include an opening for receiving the conduit to allow for left hand or right hand conduit configuration, as shown in FIG. 12. If one of the openings is not used for connection of the conduit 26, it can be covered, for example by a plate.

The side plates 70 and 72, end plates 74 and 76, rails 58 and 60, outer cover 62, inner cover 64, upper cover 66, and lower cover 68 are connected to one another to define the hollow area 52. A portion of the C-arm, and as shown the top end plate 74, ends of the side plates 70 and 72, ends of the rails 58 and 60, and ends of the upper and lower covers 66 and 68 extend past the isocenter such that the x-ray detector assembly 42 is spaced from the end of the C-arm to assist in mounting the x-ray detector assembly 42 to the body 40. Similarly, a portion of the C-arm, and as shown the bottom end plate 76, ends of the side plates 70 and 72, ends of the rails 58 and 60, and ends of the upper and lower covers 66 and 68 extend past the isocenter such that the x-ray source assembly 44 is spaced from the end of the C-arm.

Figure 13:
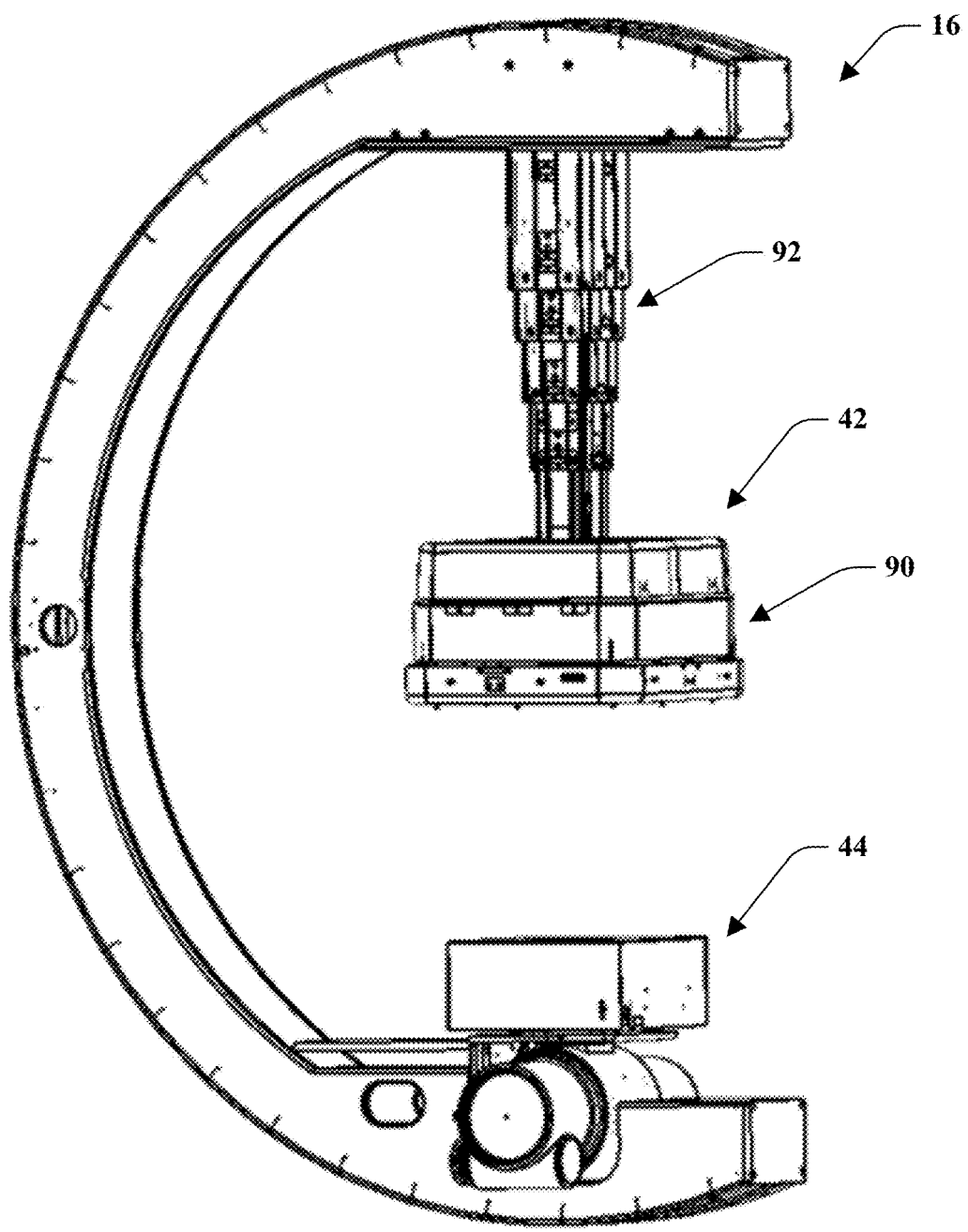
FIG. 13 is a perspective view of the exemplary imaging device with the x-ray detector assembly in an extended position.
Figure 14:
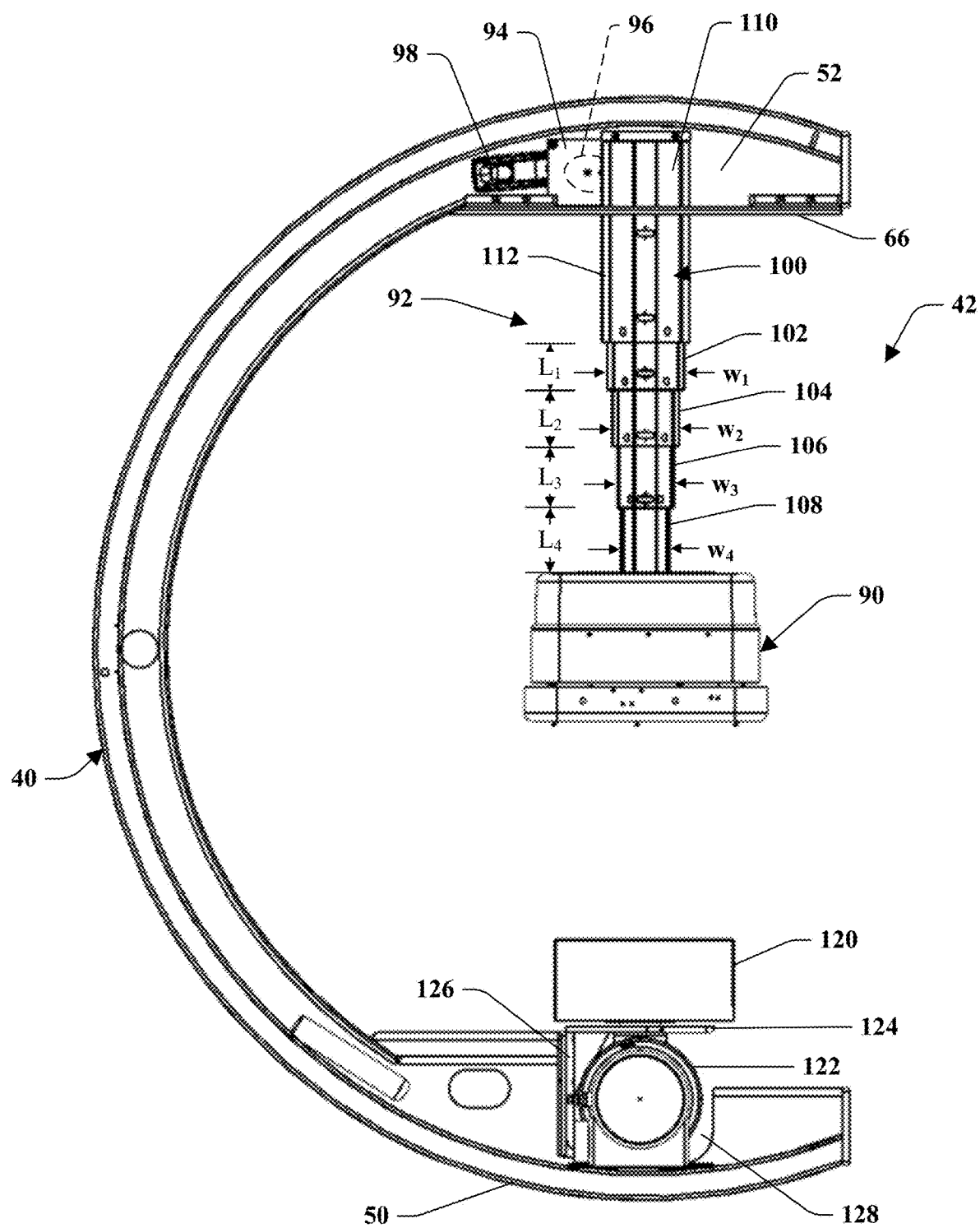
FIG. 14 is a left side view of the exemplary imaging device with the x-ray detector assembly in the extended position and a side plate removed.
Figure 15:
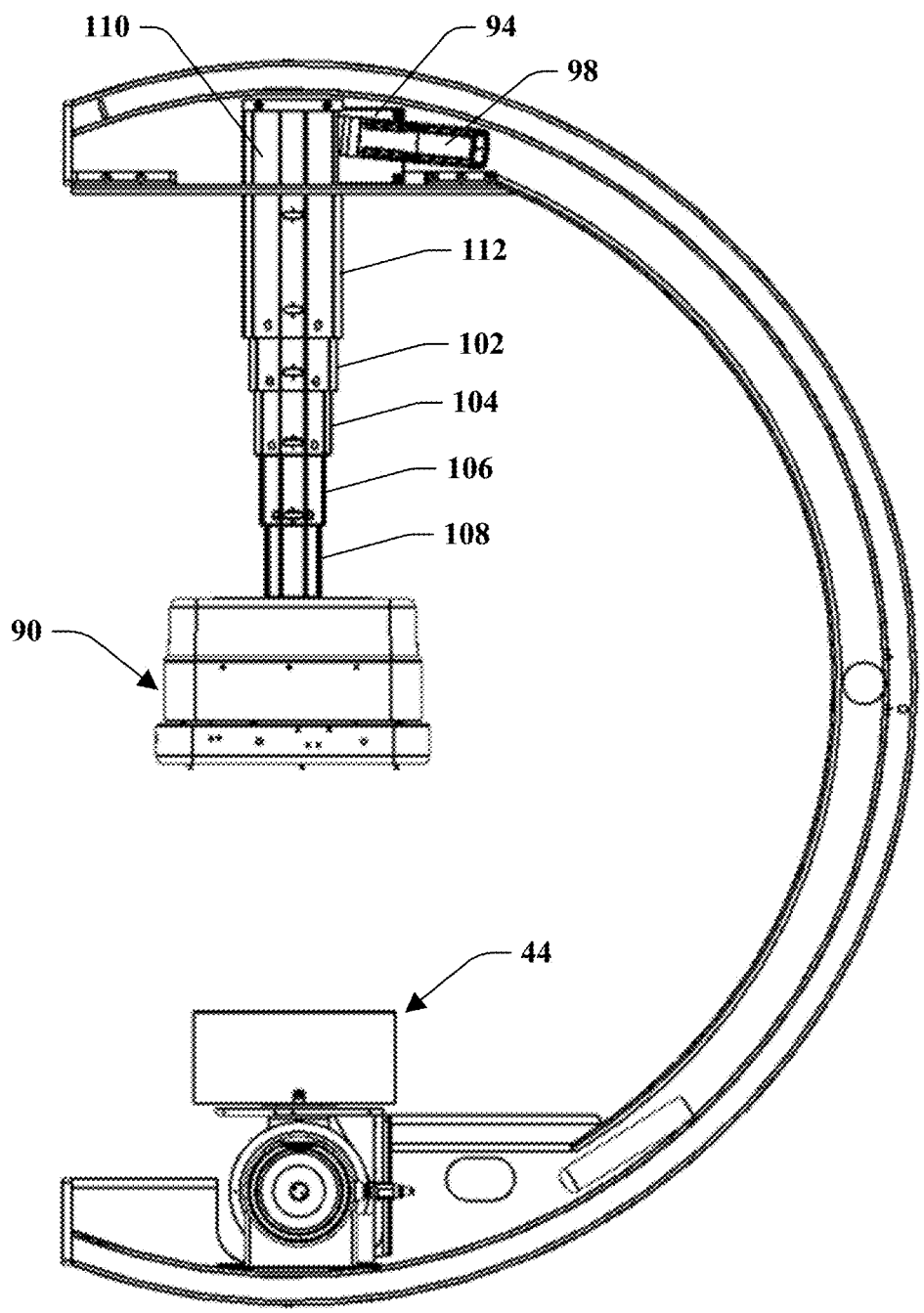
FIG. 15 is a right side view of the exemplary imaging device with the x-ray detector assembly in the extended position and a side plate removed.

Turning additionally to FIGS. 13-15, the x-ray detector assembly 42 will be discussed in detail. The x-ray detector assembly 42 includes an x-ray detector 90, a telescopic actuator 92 connected to the x-ray detector 90, a magazine 94, a chain or belt 96 housed within the magazine 94, and a motor 98. The x-ray detector 90 may be a suitable x-ray detector, such as a detector that includes a flat panel detector, an ion chamber, and an anti-scatter grid filter, and may be connected to the telescopic actuator 92 in any suitable way such that the x-ray detector 90 is inside the C-arm radius. The motor 98 may be any suitable motor, such as an electric gear motor with a brake. The motor 98 is coupled to the chain or belt to cause the chain or belt to be extended or retracted, thereby extending or retracting the telescopic actuator 92.

The telescopic actuator 92 has a first end disposed within the hollow area 52 at the upper portion 48 and a second end attached to the x-ray detector 90, and the magazine 94 and motor 98 are disposed within the hollow area 52 at the upper portion 48. To minimize a footprint of the body 40, the elements in the hollow area 52 are designed and positioned to follow the shape of the body 40. For example, as shown in FIG. 11, the motor 98 is angled relative to the magazine 94 to fit within a portion of the hollow area 52 that transitions with a curve of the body 40.

Referring now to the telescopic actuator 92 in detail, the telescopic actuator 92 includes a base telescopic section 100 and a plurality of movable telescopic sections 102, 104, 106, and 108. The base telescopic section 100 is fixed relative to the first portion 48 of the body 40 and extends toward the x-ray source 44. The plurality of movable telescopic sections 102, 104, 106, and 108 are disposed within the base telescopic section 100 in a retracted position shown in FIG. 2 and are movable relative to the base telescopic section 100 to an extended position shown in FIG. 3 and a plurality of intermediate positions therebetween. The telescopic actuator 92 allows for the range of motion of the to be multiplied to move the x-ray detector 90 between the extended and retracted positions when the body 40 is in a vertical position shown in FIGS. 2 and 3, in a horizontal position shown in FIGS. 6 and 7, and in angled positions such as the positions shown in FIGS. 8 and 9.

The base telescopic section 100 has a first portion 110 housed within the hollow area 52 and a second portion 112 disposed radially inward from the upper cover 66, and is attached to the upper cover 66 and at least one of the first and second side plates 70 and 72, for example by one or more fasteners 114 (FIG. 10). The telescopic actuator 92 is shown with four movable telescopic sections 102, 104, 106, and 108, although it will be appreciated that any suitable number of movable telescopic sections may be used provided the sizing of the movable telescopic sections fits within the base telescopic section 100, does not increase the footprint of the body 40, and maintains the rigidity to maintain the isocenter to tight tolerances. The movable telescopic sections 102, 104, 106, and 108 move relative to the base telescopic section 100 to adjust a distance between the x-ray detector 90 and the patient without moving an element beyond the outer curved surface the C-arm such that all movement of the telescopic actuator is within the inner area of the C-arm, thereby increasing the working envelop of the device without increasing the footprint. In this way, moving elements outside the C-arm that could harm a person or object in the operating room are eliminated and space is saved within the operating room.

As shown in FIG. 14, the plurality of movable telescopic sections 102, 104, 106, and 108 each have a width W1, W2, W3, W4 respectively. The width W1 of the movable telescopic section 102 adjacent the base section 100 is greater than the width W2 of the movable telescopic section 104 adjacent the movable telescopic section 102, the width W2 of the movable telescopic section 104 is greater than the width W3 of the movable telescopic section 106 adjacent the movable telescopic section 104, and the width W3 of the movable telescopic section 106 is greater than the width W4 of the movable telescopic section 108 adjacent the movable telescopic section 106 and the x-ray detector 90.

The x-ray detector 90 and the telescopic actuator 92 have little to no deflection in the extended position, for example when the body 40 is in the horizontal position and angled positions to maintain accuracy of the device, which includes maintaining the accuracy of the isocenter position with respect to all rotational axes. In an embodiment, the x-ray detector 90 deflects less than one millimeter at the total travel distance of the telescopic actuator 92 to maintain a beam of the x-ray detector 90 normal to the x-ray source assembly 44 to maintain accuracy.

The imaging device 16 is movable around a periphery of the patient to direct x-rays to an isocenter of the imaging device 16, which is shown in FIG. 2 as the intersection of the axis B-B of the x-ray detector 90 and x-ray source assembly 44 and the axis A-A of device angulation. The spatial positions of the x-ray detector 90 and the x-ray source assembly 44 can also be sensed and controlled independently and locked together in space with respect to rotation about the beam axis via a controller that receives position measurement data and maintains position control via actuators. The x-ray detector 90 and the orientation of the x-ray source or collimator can thereby be moved to a desired position and locked to a point in space with the C-arm moves as described above.

Referring now to the x-ray source assembly 44 in detail, the x-ray source assembly 44 includes a collimator 120 and an x-ray tube housed within a housing 122 and configured to be covered by the lower cover 68 as shown in FIG. 1, which may be any suitable collimator and x-ray tube. The collimator 120 and housing 122 may be attached to the body 40 in any suitable manner, such as via one or more plates 124 and 126 attached to the lower portion 50 of the body 40. As shown, the housing 122 is partially disposed in a notch 128 in the lower portion 50 of the body 40.

Although certain embodiments have been shown and described, it is understood that equivalents and modifications falling within the scope of the appended claims will occur to others who are skilled in the art upon the reading and understanding of this specification.

What is claimed is:

1. An imaging device comprising:
   a body;
   an x-ray source assembly attached to the body; and
   an x-ray detector assembly attached to the body, the x-ray detector assembly including:
      a telescopic actuator attached to and movable relative to the body, the telescopic actuator including a base section fixed relative to the body and a plurality of movable telescopic sections that are disposed within the base section in a retracted position and movable relative to the base section to an extended position and a plurality of intermediate positions therebetween, and
      an x-ray detector attached to and movable with the movable telescopic sections,
   wherein a movement axis extends through the x-ray source assembly and the x-ray detector assembly such that the plurality of movable telescopic sections, in the retracted position, the extended position, and the plurality of intermediate positions therebetween, are along the movement axis,
   wherein the plurality of movable telescopic sections each have a width, and
   wherein the width of movable telescopic section adjacent the base section is greater than the width of the movable telescopic section adjacent the x-ray imaging device, and
   wherein the body is a C-arm having a central portion configured to be attached to a pivot assembly for rotation of the C-arm, an upper portion extending from the central portion to which the telescopic actuator is attached, and a lower portion extending from the central portion to which the x-ray source is attached.

2. The imaging device according to claim 1, wherein the C-arm has an inner curved surface forming an inner surface of the central portion, the upper portion, and the lower portion, and an outer curved surface forming an outer surface of the central portion, the upper portion, and the lower portion, and wherein the telescopic actuator is attached to the upper portion such that all movement of the telescopic actuator is within an area formed within the inner curved surface.

3. The imaging device according to claim 1, wherein the x-ray detector assembly further includes a motor and a chain magazine.

4. The imaging device according to claim 3, wherein the body has a hollow area, and wherein the motor, the chain magazine, and a portion of the base section are disposed within the hollow area.

5. The imaging device according to claim 4, wherein the motor is angled relative to the chain magazine to fit within a portion of the hollow area that transitions with a curve of the body.

6. The imaging device according to claim 3, further including a chain housed within the chain magazine, wherein the motor is coupled to the chain to effect movement of the chain to thereby effect movement of the telescopic actuator between the extended and retracted positions.

7. The imaging device according to claim 1, wherein when the telescopic actuator is in the extended position and when the telescopic actuator is horizontal, the x-ray detector deflects less than one millimeter.

8. An imaging device comprising:
a C-arm having an inner curved surface and an outer curved surface;
an x-ray source assembly attached to the C-arm; and
an x-ray detector assembly attached to the C-arm, the x-ray detector assembly including a telescopic actuator aligned with the x-ray source assembly along an axis and attached to and movable relative to the C-arm along the axis, and an x-ray detector attached to and movable with the telescopic actuator along the axis, the telescopic actuator being attached to the C-arm such that all movement of the telescopic actuator is within an area formed within the inner curved surface of the C-arm.

9. The imaging device according to claim 8, wherein the telescopic actuator includes a base section fixed relative to the C-arm and at least one movable telescopic section that is disposed within the base section in a retracted position and movable relative to the base section to an extended position and a plurality of intermediate positions therebetween, and wherein the x-ray detector is attached to and movable with the at least one telescopic section.

10. The imaging device according to claim 9, wherein the at least one movable telescopic section includes a plurality of movable telescopic sections disposed within the base section in the retracted position.

11. The imaging device according to claim 10, wherein the plurality of movable telescopic sections each have a width, and wherein the width of movable telescopic section adjacent the base section is greater than the width of the movable telescopic section adjacent the x-ray imaging device.

12. The imaging device according to claim 8, wherein when the telescopic actuator is in an extended position and when the telescopic actuator is horizontal, the x-ray detector deflects less than one millimeter.

13. The imaging device according to claim 8, wherein C-arm has a central portion configured to be attached to a pivot assembly for rotation of the C-arm, an upper portion extending from the central portion to which the telescopic actuator is attached, and a lower portion extending from the central portion to which the x-ray source is attached.

14. The imaging device according to claim 8, wherein the x-ray detector assembly further includes a motor and a chain magazine.

15. The imaging device according to claim 14, wherein the body has a hollow area, and wherein the motor, the chain magazine, and a portion of the base section are disposed within the hollow area.

16. The imaging device according to claim 15, wherein the motor is angled relative to the chain magazine to fit within a portion of the hollow area that transitions with a curve of the C-arm.

17. An imaging system including:
an L-shaped attachment arm with an vertical portion and a horizontal portion;
a pivot assembly rotatably attached to the vertical portion of the L-shaped attachment arm; and
an imaging device attached to the pivot assembly, the imaging device including:
a C-arm;
an x-ray detector assembly attached to the C-arm, the x-ray detector assembly including a telescopic actuator attached to and movable relative to the C-arm and an x-ray detector attached to and movable with the telescopic actuator; and
an x-ray source assembly attached to the C-arm,
wherein a movement axis extends through the x-ray source assembly and the x-ray detector assembly such that x-ray detector is movable with the telescopic actuator along the movement axis toward and away from the x-ray source assembly.

18. The imaging system according to claim 17, wherein the telescopic actuator includes a base section fixed relative to the C-arm and a plurality of movable telescopic sections that are disposed within the base section in a retracted position and movable relative to the base section to an extended position and a plurality of intermediate positions therebetween.

19. The imaging system according to claim 18, wherein the plurality of movable telescopic sections each have a width, and wherein the width of movable telescopic section adjacent the base section is greater than the width of the movable telescopic section adjacent the x-ray imaging device.

* * * * *